US005686298A

United States Patent [19]
Patel et al.

[11] Patent Number: 5,686,298
[45] Date of Patent: Nov. 11, 1997

[54] ENZYMATIC REDUCTION METHOD FOR THE PREPARATION OF COMPOUNDS USEFUL FOR PREPARING TAXANES

[75] Inventors: Ramesh N. Patel, Bridgewater, N.J.; Amit Banerjee, Newtown, Pa.; Clyde G. McNamee, Lawrenceville, N.J.; John K. Thottathil, Robbinsville, N.J.; Laszlo J. Szarka, East Brunswick, N.J.

[73] Assignee: E. R. Squibb & Sons, Inc., Princeton, N.J.

[21] Appl. No.: 382,455

[22] Filed: Feb. 1, 1995

Related U.S. Application Data

[62] Division of Ser. No. 975,453, Nov. 12, 1992, Pat. No. 5,420,337.

[51] Int. Cl.$^6$ ...................................................... C12P 7/62
[52] U.S. Cl. ............................ 435/280; 435/135; 435/123
[58] Field of Search .................................. 435/280, 135, 435/123

[56] References Cited

U.S. PATENT DOCUMENTS

| | | |
|---|---|---|
| 4,584,270 | 4/1986 | Sih . |
| 4,601,987 | 7/1986 | Klibanov et al. . |
| 4,607,013 | 8/1986 | Mitsuda et al. . |
| 4,800,162 | 1/1989 | Matson . |
| 4,814,470 | 3/1989 | Colin et al. . |
| 4,857,468 | 8/1989 | Kutsuki ............................ 560/41 |
| 4,857,653 | 8/1989 | Colin et al. . |
| 4,876,399 | 10/1989 | Holton et al. . |
| 4,924,011 | 5/1990 | Denis et al. . |
| 4,924,012 | 5/1990 | Colin et al. . |
| 5,064,761 | 11/1991 | Schneider et al. . |
| 5,084,387 | 1/1992 | Patel et al. . |

FOREIGN PATENT DOCUMENTS

| | | |
|---|---|---|
| 0080827A2 | 6/1983 | European Pat. Off. . |
| 0266217A2 | 5/1988 | European Pat. Off. . |
| 0328125A2 | 8/1989 | European Pat. Off. . |
| 0350811A2 | 1/1990 | European Pat. Off. . |
| 0385172A1 | 9/1990 | European Pat. Off. . |
| 0400971A2 | 12/1990 | European Pat. Off. . |
| 0414610A1 | 2/1991 | European Pat. Off. . |
| 0421636A1 | 4/1991 | European Pat. Off. . |
| 9212140 | 7/1992 | WIPO . |

OTHER PUBLICATIONS

ATCC Catalogue of Bacteria, 1992, pp. 270–275.

Magri et al., J. Org. Chem. 51(6). 797–802 (1986).

Honig et al., Tetrahedron, vol. 46, No. 11, pp. 3841–3850 (1990).

Shen et al., J. Chem. Soc. Chem. Commun, pp. 677–679 (1988).

Fujisawa et al., Tetrahedron Lett., vol. 26, No. 49, pp. 6089–6092, 1985.

Chunduru et al., Biochemistry, vol. 28, No. 2, pp. 486–493, 1989.

Nieduzak, et al., Multigram Lipase–Catalyzed Enantioselective Acylation in the Synthesis of the Four Stereoisomers of a New Biologically Active α–Aryl–4–Piperidinemethanol Derivative, *Tetrahedron:Asymmetry*, vol. 2, No. 2, pp. 113–122 (1991).

Laumen, et al., A Highly Selective Ester Hydrolase from *Pseudomonas Sp.* for the Enzymatic Preparation of Enantiomerically Pure Secondary Alcohols; Chiral Auxilaries in Organic Synthesis, *J. Chem. Soc., Chem. Commun.*, pp. 598–600 (1988).

Sih, et al., The Use of Microbial Enzymes for the Synthesis of Optically Active Pharmaceuticals, *J. of Industrial Microbiology*, Suppl. No. 3, pp. 221–229 (1988).

Feichter, et al., Biocatalytic Resolution of Long–Chain 3–Hydroxy–alkanoic Esters; *Tetrahedron Letters*, vol. 30, No. 5, pp. 551–552 (1989).

Hiratake, et al., Irreversible and Highly Enantioselective Acylation of 2–Halo–1–arylethanols in Organic Solvents Catalyzed by a Lipase from *Pseudomonas fluorescens*; *J. Org. Chem.*, 53, pp. 6130–6133, (1988).

Bianchi, et al., Anhydrides as Acylating Agents in Lipase Catalyzed Stereoselective Esterification of Racemic Alcohols, *J. Org. Chem.*, 53, pp. 5531–5534 (1988).

Laumen, et al., Enantiomerically Pure Cyclohexanols and Cyclohexane–1,2–Diol Derivatives; Chiral Auxiliaries and Substitutes for (−)–8–Phenylmenthol. A Facile Enzymatic Route, *J. Chem. Soc., Chem. Commun.*, pp. 148–150 (1989).

Nakamura, et al., Stereoselective Preparation of (R)–4–Nitro–2–butanol and (R)–5–Nitro–2–pentanol Mediated by a Lipase; *Agric. Biol. Chem.*, 54(6), pp. 1569–1570 (1990).

Cambou, et al., Preparative Production of Optically Active Esters and Alcohols Using Esterase–Catalyzed Stereospecific Transesterification in Organic Media; *J. Amer. Chem. Soc.*, 106, pp. 2687–2692 (1984).

Hsu, et al., Lipase–Catalyzed Irreversible Transesterification Using Enol Esters: XAD–8 Immobilized Lipoprotein Lipase–Catalyzed Resolution of Secondary Alcohols; *Tetrahedron Letters*, vol. 31, No. 44, pp. 6403–6406 (1990).

Babiak, et al., Lipase–Catalyzed Irreversible Transesterification Using Enol Esters: Resolution of Prostaglandin Synthons 4–Hydroxy–2–alkyl–2–cyclo–pentenones and Inversion of the 4S Enantiomer to the 4R Enantiomer; *J. Org. Chem.*, 55, pp. 3377–3381 (1990).

Sih, et al., Mikrobielle asymmetrische Katalyze –enantioselektive Reduktion von Ketonen; *Angew Chem.*, 96, pp. 556–565 (1984).

Georg, et al., Asymmetric Synthesis of β–lactams and N–Benzoyl–3–Phenylisoserines via the Staudinger Reaction, *Tetrahedron Letters*, vol. 32, No. 27, pp. 3151–3154 (1991).

(List continued on next page.)

*Primary Examiner*—Irene Marx
*Attorney, Agent, or Firm*—Suzanne E. Babajko

[57] ABSTRACT

An enzymatic reduction method, particularly a stereoselective enzymatic reduction method, for the preparation of compounds useful as intermediates in the preparation of taxanes.

25 Claims, No Drawings

OTHER PUBLICATIONS

Denis, et al., An Efficient, Enantioselective Synthesis of the Taxol Side Chain, *J. Org. Chem.*, 51, pp. 46–50 (1986).

Honig, et al., Chemo–Enzymatic Synthesis of All Isomeric 3–Phenylserines and Isoserines, *Tetrahedron*, vol. 46, No. 11, pp. 3841–3850 (1990).

Fones, The Isomers of the β–phenylserines, *J. Biol. Chem.*, 204, pp. 323–328 (1953).

Denis, et al., An Improved Synthesis of the Taxol Side Chain and of RP 56976; *J. Org. Chem*, 55, pp. 1957–1959 (1990).

Ojima, et al., Efficient and Practical Asymmetric Synthesis of the Taxol C–13 Side Chain, N–Benzoyl–(2R, 3S)–3–phenylisoserine, and Its Analogues via Chiral 3–Hydroxy–4–aryl–β–lactams through Chiral Ester Enolate–Imine Cyclo–condensation, *J. Org. Chem.*, 56, pp. 1681–1683 (1991).

Imuta, et al., Product Stereospecificity in the Microbial Reduction of α–Haloaryl Ketones, *J. Org. Chem.*, 45, pp. 3352–3355 (1980).

Ohta, et al., Microbial Reduction of 1,2–Diketones to Optically Active α–Hydroxyketones; *Agric. Biol. Chem.*, 51(9), pp. 2421–2427 (1987).

Hummel, Reduction of acetophenone to R(+)–phenylethanol by a new alcohol dehydrogenase from *Lactobacillus kefir*; *Appl. Microbial Biotechnol*, 34, pp. 15–19 (1990).

Shen, et al., A New NAD–dependent Alcohol Dehydrogenase with Opposite Facial Selectivity useful for Asymmetric Reduction and Cofactor Regeneration, *J. Chem. Soc., Chem. Commun.*, pp. 677–679 (1990).

Christen, et al., Biotransformation in Organic Synthesis: Applications of Yeast Reduction in the Synthesis of 3,5–Dihydroxy Esters of High Optical Purity, *J. Chem. Soc., Chem. Commun.*, pp. 264–266 (1988).

Fujisawa, et al., Diastereo–and Enantioselective Reduction of α,β–Diketodithiane with the Baker's Yeast, *Tetrahedron Letters*, vol. 26, No. 49, pp. 6089–6092 (1985).

Willaert, et al., Enzymatic in Vitro Reduction of Ketones; *Bioorganic Chemistry*, pp. 223–231 (1988).

Hoffman, et al., Synthesis of 6S,7S–Anhydro–Serricornine, *Tetrahedron Letters*, vol. 23, No. 34, pp. 3479–3482 (1982).

Bernardi, et al., Production of (R)–1–(1, 3–Dithian–2–yl)propan–2–ol by Microbial Reduction; *J. Chem. Soc.*, Perkin Trans. I, pp. 1607–1608 (1987).

Chunduru, et al., Mechanism of Ketol Acid Reductoisomerase –Steady–State Analysis and Metal Ion Requirement, *Biochemistry*, vol. 28, No. 2, pp. 486–493 (1989).

Utaka, et al., Asymmetric Reduction of a Prochiral Carbonyl Group of Aliphatic γ and δ–Keto Acids by Use of Fermenting Bakers' Yeast, *J. Org. Chem.*, vol. 52, pp. 4363–4368 (1987).

Dale, et al., α–Methoxy–α–trifluoromethylphenylacetic Acid, a Versatile Reagent for the Determination of Enantiomeric Composition of Alcohols and Amines; *The J. of Org. Chem.*, vol. 34, No. 9, pp. 2543–2550 (1969).

Naoshima, et al., Biotransformation of Some Keto Esters through the Consecutive Reuse of Immobilized *Nicotiana tabacum* Cells; *J. Org. Chem.*, vol. 54, pp 4237–4239 (1989).

Bucciarelli, et al. Asymmetric Reduction of Trifluoromethyl and Methyl Ketones by Yeast; An Improved Method; *Synthesis Communications*, pp. 897–899 (1983).

Charles, et al., Bicyclic Heterocycles with Nitrogen at the Ring Junction. Part 2. Application of the Dakin–West Reaction to the Synthesis of Imidazo[5,1-f]–1,2, 4–triazin–4(3H)–ones, *J.C.S. Perkin I*, pp. 1139–1145 (1980).

Denis, et al., A Highly Efficient, Practical Approach to Natural Taxol, *J. Am. Chem. Soc.*, 110, 5917–5919 (1988).

Deng et al., A Practical, Highly Enantioselective Synthesis of the Taxol Side Chain via Asymmetric Catalyst; *J. Org. Chem.*, 57, pp. 4320–4323 (1992).

Holton, et al., A Synthesis of Taxusin, *J. Am. Chem. Soc.*, 110, pp. 6558–6560 (1988).

Angelastro et al., *J. Med. Chem.*, 33(1), pp. 11–13 (1990).

ENZYMATIC REDUCTION METHOD FOR THE PREPARATION OF COMPOUNDS USEFUL FOR PREPARING TAXANES

This is a division of application Ser. No. 07/975,453, filed Nov. 12, 1992 now U.S. Pat. No. 5,420,337.

FIELD OF THE INVENTION

The present invention relates to an enzymatic reduction method for the preparation of compounds useful as intermediates in the preparation of taxanes, and particularly to the stereoselective preparation of such compounds.

BACKGROUND OF THE INVENTION

Taxanes are diterpene compounds which find utility in the pharmaceutical field. For example, taxol, a taxane having the structure:

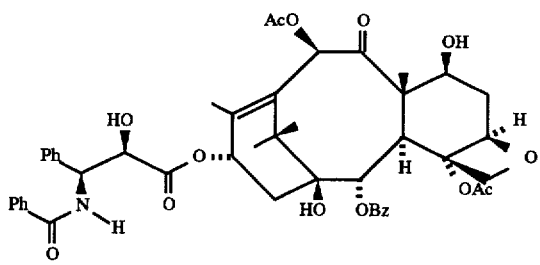

where Ph is phenyl, Ac is acetyl and Bz is benzoyl, has been found to be an effective anticancer agent.

Naturally occurring taxanes such as taxol may be found in plant materials, and have been isolated therefrom. Such taxanes may, however, be present in plant materials in relatively small amounts so that, in the case of taxol, for example, large numbers of the slow-growing yew trees forming a source for the compound may be required. The art has thus continued to search for synthetic, including semi-synthetic routes for the preparation of taxanes, such as taxol and analogs thereof, as well as routes for the preparation of intermediates used in the preparation of these compounds. Methods allowing efficient preparation of chiral intermediates, providing final taxane products having a desired stereoconfiguration, are particularly sought.

SUMMARY OF THE INVENTION

The present invention provides a method for the enzymatic reduction, preferably, the stereoselective enzymatic reduction, of keto group-containing compounds to form hydroxyl group-containing stereoisomers useful as intermediates in the preparation of taxanes such as taxol.

Specifically, the present invention provides a method for the enzymatic reduction of a compound of the formula I or a salt thereof:

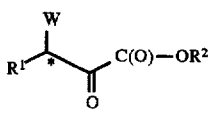

to form a compound of the formula II or a salt thereof:

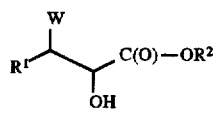

where
W is
  (a) —$NHR^3$; or
  (b) —$N_3$;
$R^1$ is
  (a) aryl;
  (b) alkyl;
  (c) alkenyl; or
  (d) alkynyl;
$R^2$ is
  (a) hydrogen; or
  (b) $R^4$;
$R^3$ is
  (a) hydrogen;
  (b) $R^4$;
  (c) —C(O)—$OR^4$; or
  (d) —C(O)—$R^4$; and
$R^4$ is
  (a) alkyl;
  (b) aryl;
  (c) cycloalkyl;
  (d) alkenyl;
  (e) alkynyl;
  (f) cycloalkenyl; or
  (g) heterocyclo;
where, with respect to the chiral center marked with an asterisk, said compound of the formula I may be present as a single isomer or as a mixture of both R and S isomers (for example, as a racemate),
comprising the step of contacting said compound of the formula I or salt thereof with an enzyme or microorganism capable of catalyzing said reduction, and effecting said reduction.

In a preferred embodiment of the present invention, the compound of the formula I or salt thereof is reduced to preferentially form the following compounds IIa and/or IIb or salts thereof:

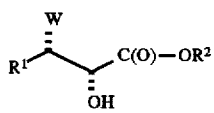

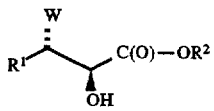

A particularly preferred embodiment of the present invention provides a method for the stereoselective enzymatic reduction of a compound of the formula I or salt thereof to form a compound of the formula IIa or IIb or a salt thereof, comprising the step of contacting said compound of the formula I or salt thereof with an enzyme or microorganism capable of catalyzing said stereoselective reduction, and effecting said reduction.

DETAILED DESCRIPTION OF THE INVENTION

The methods of the present invention are described further as follows.

In the compounds of formula II, the group W and the hydroxyl group are bonded to asymmetric carbon atoms. Thus, the following four stereoisomers may be formed as the compound of the formula II:

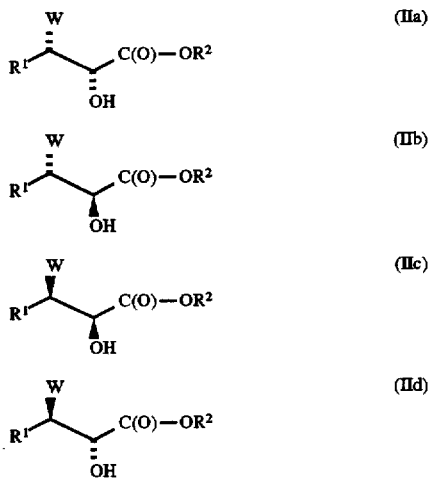

As used herein, "preferential" formation of the compounds of the formulae IIa and/or IIb denotes the formation of one or both of these compounds preferentially relative to formation of the compounds of the formulae IIc and/or IId.

The terms "stereoselective enzymatic reduction" and "stereoselective reduction", as used herein, refer to the preferential formation of a single enantiomer of the compound of the formula II (that is, IIa, IIb, IIc or IId) relative to other stereoisomers thereof. Thus, for example, stereoselective reduction of the compound of the formula I to form a compound of the formula IIa denotes prefential formation of the compound of the formula IIa relative to the formation of compounds of the formulae IIb, IIc and IId. Stereoselective reduction of the compound of the formula I to form a compound of the formula IIb denotes preferential formation of the compound of the formula IIb relative to compounds of the formulae IIa, IIc and IId.

Compounds of the formula IIa have the same absolute stereoconfiguration, at the carbon atom bearing the group W and the carbon atom bearing the hydroxyl group formed by the reduction process, as the compound (2R,3S)-(−)-N-benzoyl-3-phenylisoserine ethyl ester. Compounds of the formula IIb have the same absolute stereoconfiguration at the corresponding carbon atoms as the compound (2S,3S)-(−)-N-benzoyl-3-phenylisoserine ethyl ester.

With respect to the chiral center marked with an asterisk, the starting compound of formula I may be present as a single isomer having the R or S configuration, or as a mixture of the R and S isomers, for example, as a racemate.

The term "mixture", as said term is used herein in relation to stereoisomeric, such as enantiomeric compounds, includes mixtures having equal (i.e. racemic for an enantiomeric mixture) or non-equal amounts of stereoisomers.

The terms "enzymatic process" or "enzymatic method", as used herein, denote a process or method of the present invention employing an enzyme or microorganism.

The terms "alkyl" or "alk", as used herein alone or as part of another group, denote optionally substituted, straight and branched chain saturated hydrocarbon groups, preferably having 1 to 10 carbons in the normal chain. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include one or more of the following groups: halo, alkoxy, alkylthio, alkenyl, alkynyl, aryl, cycloalkyl, cycloalkenyl, hydroxy or protected hydroxy, carboxyl (—COOH), alkyloxycarbonyl, alkylcarbonyloxy, carbamoyl ($NH_2$—CO—), amino (—$NH_2$), mono- or dialkylamino, or thiol (—SH).

The terms "lower alk" or "lower alkyl" as used herein, denote such optionally substituted groups as described above for alkyl having 1 to 4 carbon atoms in the normal chain.

The terms "alkoxy" or "alkylthio" denote an alkyl group as described above bonded through an oxygen linkage (—O—) or a sulfur linkage (—S—), respectively. The term "alkyloxycarbonyl", as used herein, denotes an alkoxy group bonded through a carbonyl group. The term "alkylcarbonyloxy", as used herein, denotes an alkyl group bonded through a carbonyl group which is, in turn, bonded through an oxygen linkage. The terms "monoalkylamino" or "dialkylamino" denote an amino group substituted by one or two alkyl groups as described above, respectively.

The term "alkenyl", as used herein alone or as part of another group, denotes such optionally substituted groups as described above for alkyl, further containing at least one carbon to carbon double bond.

The term "alkynyl", as used herein alone or as part of another group, denotes such optionally substituted groups as described above #or alkyl, further containing at least one carbon to carbon triple bond.

The term "cycloalkyl", as used herein alone or as part of another group, denotes optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The term "cycloalkenyl", as used herein alone or as part of another group, denotes such optionally substituted groups as described above for cycloalkyl, further containing at least one carbon to carbon double bond forming a partially unsaturated ring.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include phenyl, biphenyl, and naphthyl. Exemplary substituents include one or more, preferably three or fewer, nitro groups, alkyl groups as described above or groups described above as alkyl substituents.

The terms "heterocyclo" or "heterocyclic", as used herein alone or as part of another group, denote optionally substituted fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom of the ring system. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, and benzofurazanyl. Exemplary substituents include one or more alkyl groups as described above or one or more groups described above as alkyl substituents.

The terms "halogen" or "halo", as used herein alone or as part of another group, denote chlorine, bromine, fluorine, and iodine.

The term "taxane moiety", as used herein, denotes moieties containing the core structure:

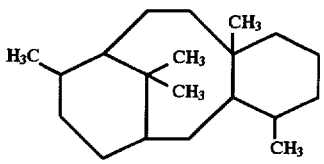

which core structure may be substituted and which may contain ethylenic unsaturation in the ring system thereof.

The term "taxane", as used herein, denotes compounds containing a taxane moiety as described above.

The term "hydroxy protecting group", as used herein, denotes any group capable of protecting a free hydroxyl group which, subsequent to the reaction for which it is employed, may be removed without disturbing the remainder of the molecule. Such groups, and the synthesis thereof, may be found in "Protective Groups in Organic Synthesis" by T. W. Greene, John Wiley and Sons, 1981, or Fieser & Fieser. Exemplary hydroxyl protecting groups include methoxymethyl, 1-ethoxyethyl, 1-methoxy-1-methylethyl, benzyloxymethyl, (β-trimethylsilylethoxy)methyl, tetrahydropyranyl, 2,2,2-trichloroethoxycarbonyl, t-butyl (diphenyl)silyl, trialkylsilyl, trichloromethoxycarbonyl, and 2,2,2-trichloroethoxymenhyl.

The term "salt" includes acidic and/or basic salts formed with inorganic and/or organic acids and bases.

STARTING MATERIALS

The starting materials employed in the present reduction method may be obtained according to the following Reaction Scheme, and as described by Charles et al., J. C. S. Perkin I, 1139 (1980).

Reaction Scheme

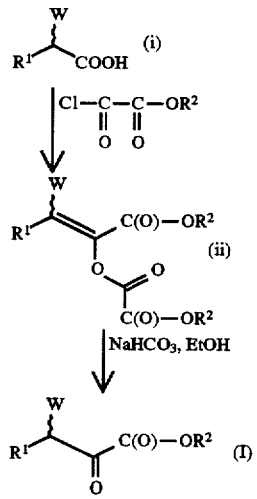

According to the above Reaction Scheme, compounds of the formula I may be prepared by reacting a compound (i) with an oxalyl chloride ester of the formula Cl —C(O)—C (O)—OR², where R² is preferably unsubstituted lower alkyl such as ethyl or methyl, for example, in anhydrous tetrahydrofuran (THF) in the presence of 4-dimethylaminopyridine (DMAP) and pyridine, to form a compound (ii). compounds of the formula (i) and esters of the formula Cl —C(O)—C (O)—OR² are commercially available or may readily be prepared by one of ordinary skill in the art. In the compound (i), w is preferably an amide group —NH—C(O)—R⁴, such as benzoylamino, or a urethane group —NH—C(O)—OR⁴, such as where R⁴ is unsubstituted alkyl (for example, the urethane group t-butyloxycarbonylamino (BOC)), which may be prepared by reacting the corresponding compound (i) where W is amino (—NH₂) with the reagent R⁴—C(O) —Cl or [R⁴—C(O)]₂O.

A racemate of a compound of the formula I may then be prepared from the compound (ii), for example, by heating the compound (ii) in ethanol in the presence of anhydrous NaHCO₃ or other mild bases. Starting materials which are other than racemic may be obtained, for example, by separation of the isomers of the racemate prepared above, or by addition of one or both of the enantiomers of the compound of formula I in unequal portions to a racemic mixture thereof.

The present invention provides novel compounds of the formula (ii), where R¹, R² and W are as defined above, except that, when W is —NH—C(O)—R⁴ and R² is ethyl, (1) R⁴ is not isobutyl, n-propyl, cyclopentyl or phenyl when R¹ is methyl, and (2) R⁴ is not n-propyl when R¹ is phenyl. Preferably, in the compounds of the formula (ii), R¹ is aryl such as phenyl, W is arylcarbonylamino such as benzoylamino or alkyloxycarbonylamino such as t-butyloxycarbonylamino (BOC), and R² is alkyl such as unsubstituted lower alkyl (e.g. methyl or ethyl). All stereoisomers, such as cis- and transisomers, of the novel compounds of the formula (ii), alone or in admixture, are contemplated.

The present invention also provides novel compounds of the formula I, where R¹, R² and W are as defined above, except that, when W is —NH—C(O)—R⁴ and R² is ethyl, (1) R⁴ is not isobutyl, n-propyl, cyclopennyl or phenyl when R¹ is methyl, and (2) R⁴ is not n-propyl when R¹ is phenyl. Preferably, in the compounds of the formula I, R¹ is aryl such as phenyl, W is arylcarbonylamino such as benzoylamino or alkyloxycarbonylamino such as t-butyloxycarbonylamino, and R² is alkyl such as unsubstituted lower alkyl (e.g. methyl or ethyl). All stereoisomers of the novel compounds of the formula I, alone or in admixture (e.g. racemates), are contemplated.

PREFERRED COMPOUNDS

It is preferred to prepare, according to the present invention, compounds of the formula II in which: W is —NHR³, R¹ is aryl, especially phenyl, R² is alkyl, especially unsubstituted lower alkyl such as ethyl or methyl, and R³ is arylcarbonyl, especially benzoyl, or alkyloxycarbonyl, especially t-butyloxycarbonyl. It is further preferred to stereoselectively prepare compounds of the formula IIa or IIb.

ENZYMES AND MICROORGANISMS

The enzyme or microorganism employed in the present invention may be any enzyme or microorganism capable of catalyzing the enzymatic reduction, preferably the stereoselective enzymatic reduction, described herein. The enzymatic or microbial materials may be employed in the free state or immobilized on a support such as by physical adsorption or entrapment.

Suitable enzymes, regardless of origin or purity, include those enzymes referred to as oxido-reductases or dehydrogenases. The enzyme employed may, for example, be an enzyme isolated from a microorganism such as by homogenizing cell suspensions, followed by disintegration, centrifugation, DEAE-cellulose chromatography, ammonium sulfate fractionation, chromatography using gel filtration media such as Sephacryl (cross-linked co-polymer of allyl dextran and N,N'-methylene bisacrylamide) chromatography, and ion exchange chromatography such as Mono-Q (anion exchanger which binds negatively charged biomolecules through quaternary amine groups) chromatography. Exemplary such enzymes include L-2-hydroxyisocaproate dehydrogenase, lactic acid dehydrogenase, yeast enzyme concentrate (may be obtained from Sigma), β-hydroxybutyrate dehydrogenase, glucose dehydrogenase, alcohol dehydrogenase, glycerol dehydrogenase, formate dehydrogenase, pyruvate dehydrogenase, hydroxy steroid dehydrogenase, and those enzymes derived from the microorganisms described following.

With respect to the use of microorganisms, the methods of the present invention may be carried out using any suitable microbial materials capable of catalyzing the enzymatic reduction, preferably the stereoselective enzymatic reduction, described herein. For example, the cells may be used in the form of intact wet cells or dried cells such as lyophilized, spray-dried or heat-dried cells, or in the form of treated cell material such as ruptured cells or cell extracts. Suitable microorganisms include genera from bacteria, yeasts and fungi such as Achromobacter, Acinetobacter, Actinomyces, Alkaligenes, Arthrobacter, Azotobacter, Bacillus, Brevibacterium, Corynebacterium, Flavobacterium, Methylomonas, Mycobacterium, Nocardia, Pseudomonas, Rhodococcus, Streptomyces, Xanthomonas, Aspergillus, Candida, Fusarium, Geotrichum, Hansenula, Kloeckera, Penicillium, Pichia, Rhizopus, Rhodotorula, Saccharomyces, Trichoderma, Mortierella, Cunninghamella, Torulopsis, Mucor and Rhodopseudomonas.

The use of genetically engineered organisms is also contemplated. The host cell may be any cell, e.g. *Escherichia coli*, modified to contain a gene or genes for expressing one or more enzymes capable of catalysis as described herein.

Preferred microorganisms include *Arthrobacter simplex, Nocardia restricta, Rhodococcus fascians, Mycobacterium vacca, Nocardia meditteranei, Nocardia autotrophica, Rhodococcus equi, Candida albicans, Pichia pastoris, Pichia metchanolica, Torulopsis polysporium, Torulopsis glabrata* and *Acinetobacter calcoaceticus*, and especially *Mortierella alpina* (e.g. ATCC 32221), *Nocardia globerula* (e.g. ATCC 21505), *Cunninghamella echinulata* (e.g. ATCC 26269), *Nocardia salmonicolor* (e.g. ATCC 19149), *Geotrichum candidum* (e.g. ATCC 34614), *Candida guilliermondii* (e.g. ATCC 20318 and ATCC 9058), *Aspergillus versicolor* (e.g. ATCC 26268), *Penicillium thomii* (e.g. ATCC 14974), *Rhodococcus erythropolis* (e.g. ATCC 4277), *Rhodococcus rhodochrous* (e.g. ATCC 19150 and ATCC 14341), *Saccharomyces cerevisiae* (e.g. ATCC 24702), *Pseudomonas putida* (e.g. ATCC 11172), *Mortierella ramanniana* (e.g. ATCC 38191), *Mucor hiemalis* (e.g. ATCC 8977B), *Pichia pinus* (e.g. ATCC 28780), *Hansenula anomala* (e.g. ATCC 8170), *Hansenula fabiannii* (e.g. ATCC 58045) and *Hansenula polymorpha* (e.g. ATCC 26012).

Particularly preferred organisms for the preparation of compounds of the formula IIa are microorganisms of the species *Hansenula polymorpha*, especially the strain *Hansenula polymorpha* ATCC 26012, and the species *Hansenula fabiannii*, especially the strain *Hansenula fabiannii* ATCC 58045. It is also particularly preferred to employ cell extracts or isolated enzymes from these organisms.

The term "ATCC" as used herein refers to the accession number of the American Type Culture Collection, 12301 Parklawn Drive, Rockville, Md. 20852, the depository for the organism referred The enzymatic reduction method of the present invention may be carried out subsequent to the fermentation of the microorganism employed (two-stage fermentation and reduction), or concurrently therewith, that is, in the latter case, by in situ fermentation and reduction (single-stage fermentation and reduction). In the single-stage process, the microorganisms may be grown in an appropriate medium until sufficient growth of the microorganisms is attained. A compound of the formula I may then be added to the microbial cultures and the enzymatic reduction continued with the fermentation, preferably until complete conversion is obtained.

In the two-stage process, the microorganisms may, in the first stage, be grown in an appropriate medium for fermentation until exhibiting the desired enzymatic (e.g. oxidoreductase) activity. Subsequently, the cells may be harvested by centrifugation and microbial cell suspensions prepared by suspending harvested cells in an appropriate buffered solution. Buffers such as tris-HCl, phosphates, sodium acetate and the like may be used. Water may also be used to prepare suspensions of microbial cells. In the second stage, the compound I may be mixed with the microbial cell suspensions, and the enzymatic reduction of compound I catalyzed by the microbial cell suspensions. The reduction is preferably conducted until all or nearly all of the compound I is reduced.

Growth of the microorganisms may be achieved by one of ordinary skill in the art by the use of an appropriate medium. Appropriate media for growing microorganisms include those which provide nutrients necessary for the growth of the microbial cells. A typical medium for growth includes necessary carbon sources, nitrogen sources, and trace elements. Inducers may also be added. The term "inducer", as used herein, includes any compound enhancing formation of the desired enzymatic (e.g. oxido-reductase) activity within the microbial cell, such as those compounds containing keto groups. Formula I compounds may be added as inducers during growth of the microorganisms.

Carbon sources may include sugars such as maltose, lactose, glucose, fructose, glycerol, sorbitol, sucrose, starch, mannitol, propylene glycol, and the like; organic acids such as sodium acetate, sodium citrate, and the like; amino acids such as sodium glutamate and the like; and alcohols such as ethanol, propanol and the like.

Nitrogen sources may include N—Z amine A, corn steep liquor, soy bean meal, beef extracts, yeast extracts, molasses, baker's yeast, trylptone, nutrisoy, peptone, yeastamin, sodium nitrate, ammonium sulfate and the like.

Trace elements may include phosphates and magnesium, manganese, calcium, cobalt, nickel, iron, sodium and potassium salts.

The medium employed may include more than one carbon or nitrogen source or other nutrient.

Preferred media include aqueous media containing the following (in weight %):

| Medium 1 | |
|---|---|
| Malt Extract | 1% |
| Yeast Extract | 1% |
| Peptone | 1% |
| Glucose | 2% |
| | pH 7.0 |
| Medium 2 | |
| Peptone | 0.3% |
| Glycerel | 44 |
| Malt Extract | 1% |
| Yeast Extract | 1% |
| | pH 7.0 |
| Medium 3 | |
| Peptone | 0.3% |
| Fructose | 2% |
| Malt Extract | 1% |
| Yeast Extract | 1% |
| | pH 7.0 |
| Medium 4 | |
| Sodium Succinate | 2% |
| Malt Extract | 1% |
| Yeast Extract | 1% |
| Peptone | 0.3% |
| | pH 7.0 |

The pH of the medium is preferably adjusted to about 6 to 8, most preferably to 6.5, sterilized, e.g. at a temperature of 121° C. for 30 minutes, and then adjusted to a pH of about 6.5 to 7.5, preferably 7.0, after sterilization. The pH of the medium is preferably maintained between 4.0 and 9.0, most preferably between 6.0 and 8.0, during the growth of microorganisms and during the reduction process.

Temperature is a measure of the heat energy available for the reduction process, and should be maintained to ensure that there is sufficient energy available for this process. A suitable temperature range is from about 15° C. to about 60° C. A preferred temperature range is from about 25° C. to about 40° C.

The agitation and aeration of the reaction mixture affects the amount of oxygen available during the reduction process, which may be conducted, for example, in shake-flask cultures or fermentor tanks during growth of microorganisms in a single-stage or two-stage process. The agitation range from 50 to 1000 RPM is preferable, with 50 to 500 RPM being most preferred. Aeration of about 0.1 to 10 volumes of air per volume of media per minute (i.e., 0.1 to 10 v/vt) is preferred, with aeration of about 5 volumes of air per volume of media per minute (i.e., 5 v/vt) being most preferred.

Complete conversion of the compound I may take, for example, from about 12 to 48 hours, such as 4 to 24 hours, measured from the time of initially treating the compound I with a microorganism or enzyme as described herein.

The enzymatic reduction method of the present invention may be carried out using a co-factor such as nicotinamide adenine dinucleotide (NADH), especially when an isolated enzyme is employed. NADH, for example, may thereafter be regenerated and reused. A further enzyme that regenerates the NADH in situ may be employed such as formate dehydrogenase. Suitable hydrogen donors include molecular hydrogen, a formate (e.g. an alkali metal or ammonium formate), a hypophosphite or an electrochemical reduction in the presence of a viologen, for example methyl viologen. It is also possible to regenerate NADH without further enzymes using, for example, ethanol or formate.

It is preferred to employ an aqueous liquid as the reaction medium, although an organic liquid, or a miscible or immiscible (biphasic) organic/aqueous liquid mixture may also be employed.

It is preferred to employ 0.1 to 25 weight % of the compound I starting material based on the combined weight of compound I and reaction medium. The amount of enzyme or microorganism employed relative to the starting material is selected to allow catalysis of the enzymatic reduction of the present invention.

It is preferred to employ parameters, such as enzymes and microorganisms, which provide a stereoselective reduction. A stereoselective reduction is advantageous in that an efficient conversion of substrate may be achieved, and in that the procedures which may be employed in the subsequent separation of the desired enantiomer of the formula II from the remaining components of the reaction medium may be minimized. It is particularly preferred to employ parameters which provide a reaction yield greater than about 80%, most preferably greater than about 90%, and an optical purity greater than about 90%, most preferably greater than about 99%, of a desired enantiomer of the formula II. To obtain stereoselective reduction of the substrate compound I, it is desirable to employ the enzymes and microorganisms indicated above as preferred.

SEPARATION

The products of the reduction process of the present invention may be isolated and purified, for example, by methods such as extraction, distillation, crystallization, and column chromatography.

For example, a preferred method for separating the compound IIa from the remaining components of the reaction medium is by extraction. An exemplary extraction technique, such as where (2R,3S)-(−)-N-benzoyl-3-phenylisoserine ethyl ester is prepared by whole cell suspensions, is that where the reaction medium, containing the aforementioned suspensions, is extracted with ethyl acetate, the organic layer is washed with brine, and the solvent is then removed under reduced pressure to generate an oily liquid which is chromatographed on silica to produce the desired product compound IIa.

Taxanes are diterpene compounds containing the taxate moiety:

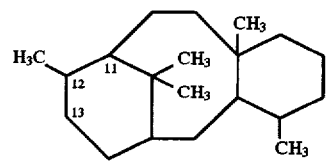

described above. Of particular interest are taxanes containing a taxane moiety in which the 11,12-positions are bonded through an ethylenic linkage, and in which the 13-position contains a sidechain, which taxanes are exemplified by taxol. Pharmacologically active taxanes such as taxol may be used as antitumor agents to treat patients suffering from cancers such as breast, ovarian, colon or lung cancers, melanoma and leukemia.

The compounds of the formula II obtained by the reduction method of the present invention are particularly useful as intermediates in forming the aforementioned sidechain on the taxate moiety. The addition of such a sidechain, in and of itself, may impart an increased or more desirable pharmacological activity to the taxate product, or may form a taxane product which is more readily converted to a taxane having an increased or more desirable pharmacological activity than the starting compound.

The compounds of the formula II prepared according to the reduction method of the present invention may optionally be modified prior to use in sidechain formation. For example, compounds containing an azide group (N₃) as the group W may be treated with a reducing agent to form an amine group, the latter which may be substituted to form the group —NHR³.

The compounds of the formula II obtained by the method of the present invention may, for example, be used in the preparation of sidechain-bearing taxanes such as those described in European Patent Publication No. 400,971, U.S. Pat. Nos. 4,876,399, 4,857,653, 4,814,470, 4,924,012, and 4,924,011, all incorporated herein by reference.

For example, taxanes bearing a hydroxyl group at C-13, such as those described in the aforementioned European Patent Publication No. 400,971, may be coupled with an optionally modified compound of the formula II in the presence of a condensing agent, for example, a carbodiimide such as dicyclohexylcarbodiimide or a reactive carbonate such as di-2-pyridyl carbonate, as well as a tertiary amine activating agent, for example, a dialkylaminopyridine such as 4-dimethylaminopyridine. An inert solvent such as benzene, toluene, a xylene, ethylbenzene, isopropylbenzene or chlorobenzene, and a temperature of from about 60° C. to about 90° C., may be employed.

Coupling may be conducted as described by Ojima et al., *J. org. Chem.*, 56, 1681 (1991), incorporated herein by reference. See also Denis et al., *J. Am. Chem. Soc.*, 110, 5917 (1988), also incorporated herein by reference. Taxol is preferably ultimately prepared as the sidechain-bearing taxane.

Salts or solvates such as hydrates of reactants or products may be employed or prepared as appropriate in any of the methods of the present invention.

The present invention is further described by the following examples which are illustrative only, and are in no way intended to limit the scope of the instant claims.

EXAMPLE 1

Preparation of Startina Material and Enzymatic Reduction

Preparation of 2-Keto-3-(N-benzoylamino)-3-phenylpropionic acid ethyl ester: Racemic starting material (a) Benzoyl phenylglycine

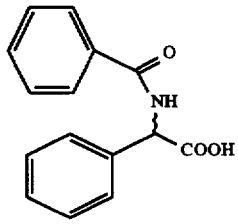

To (DL)-phenylglycine (9 g, 60 mmole) in aqueous NaOH (1N, 180 ml) at 0° C. was added dropwise neat benzoyl chloride (PhCOCl) (7.73 ml, 66 mmole) over a period of 5 minutes. The resulting solution was stirred for an additional 1 hour. The reaction solution was washed with ethyl acetate (EtOAc) (20 ml×2), then neutralized by 6N HCl and extracted with EtOAc (60 ml×2). The combined EtOAc layer was washed with brine (30 ml×2), dried over MgSO₄, filtered and concentrated to give a residue. The residue was crystallized from EtOAc/hexane to give 10.65 g of benzoyl phenylglycine as a white solid (70% yield, first crops). (The title product is also commercially available.)

(b) 3-Benzoylamino-3-phenyl-(ethyl, 2-oxalyl) propenoic acid, ethyl ester

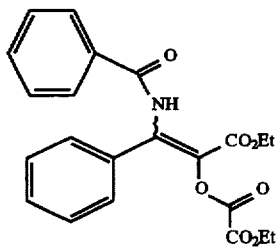

To a stirred solution of benzoyl phenylglycine prepared in step (a) (6.12 g, 24 mmole), 4-dimethylaminopyridine (100 mg, 0.82 mmole), and pyridine (5.86 ml, 72 mmole) in anhydrous tetrahydrofuran (THF) (24 ml) was added ethyl oxalyl chloride (5.35 ml, 48 mmole) at a rate to initiate gentle refluxing. (Refluxing at this point was not critical when sufficient refluxing (~3.5 h) as followed was employed). The mixture was then heated to maintain a gentle reflux for 3.5 hours. The reaction was monitored by thin layer chromatography (TLC) using 30% EtOAc in hexane as eluent ($R_f$ for the starting material was on the base line and $R_f$ for the products were 0.50 and 0.63 (E and Z isomers)). After cooling, the room temperature mixture was treated with water (48 ml) and stirred vigorously at room temperature for ½ hour. The resulting organic layer was separated and the aqueous layer was extracted with EtOAc (36 ml×2). The combined organic layer was washed with brine (30 ml×1), dried over Na₂SO₄, filtered, concentrated, and crystallized from EtOAc/hexane to obtain 4.68 g of the enol ester title product (~63% yield, first crop—no attempt was made to get a second crop.)

(c) Racemic 2-Keto-3-(N-benzoylamino)-3-phenylpropionic acid ethyl ester

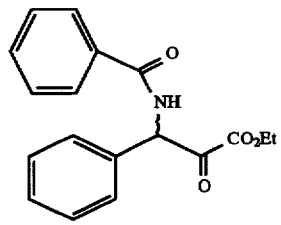

To a suspension of the enol ester title product prepared in step (b) above (6.0 g, 14.6 mmole) in 20 ml ethanol (EtOH) was added anhydrous NaHCO₃ (0.8 g, 9.49 mmole). The reaction mixture was refluxed for ½ hour. The reaction was monitored by TLC using 2% acetone in CH₂Cl₂ as eluent ($R_f$ for the starting materials were 0.50 and 0.75 (E & Z isomers) and $R_f$ for the product was 0.41). NaHCO₃ was filtered (if any) and the filtrate was concentrated to an oil. It was purified by column chromatography ((CO₂Et)₂ was removed by column chromatography) (2% acetone/CH₂Cl₂) to give 5.6 g of the title product (~100% yield). (Crystallization was used for purification in subsequent preparation of the title product.) When the compound was stored in the freezer, it solidified.

m.p.: 80°–83° C.
TLC: $R_f$=0.43; Silica gel; 2% Acetone in CH₂Cl₂; UV and PMA Visualization.

Enzymatic Reduction: Use of Various Strains of Whole Cells

The substrate for the following enzymatic reduction process was racemic 2-keto-3-(N-benzoylamino)-3- phenylpropionic acid ethyl ester ("Compound A") having the structure set forth above. Of particular interest in this example was preparation of the compound having the following structure:

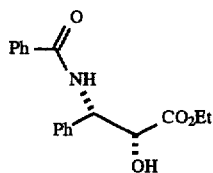

and the name (2R,3S)-(−)-N-benzoyl-3-phenylisoserine ethyl ester ("Compound B"). The microorganisms which were employed in the reduction process are listed in Table 1 following.

The microorganisms employed were maintained in a vial in liquid nitrogen. For routine development of inoculum, one vial was inoculated into 100 ml of Medium 1 (see above for the composition thereof) in a 500 ml flask and incubated at 28° C. and 280 RPM on a shaker for 48 hours. After growth of the microorganism, 10 ml of culture was inoculated into a 500 ml flask containing 100 ml of Medium 1 and incubated at 28° C. and 250 RPM on a shaker.

Cells were harvested and suspended in 100 mM potassium phosphate buffer pH 6.0. 10 ml of 20% w/v cell-suspensions were prepared. Cell-suspensions were supplemented with 25 mg of substrate (Compound A) and 750 mg of glucose and the reductions ("biotransformations") were conducted at 25° C., 150 RPM for 72 hours. One volume of sample was taken and extracted with two volumes of ethyl acetate and the separated organic phase was filtered through a 0.2 µm LID/x filter and collected.

Samples were analyzed for substrate and product concentration by a Hewlett Packard 1070 HPLC System. A Phenomenex Cyanopropyl Column (150×4.6 mm, 5µ) was used. The mobile phase consisted of 5% isopropanol in hexane. The flow rate was 0.5 ml/min at ambient temperature. The detection wavelength was 230 nm. The retention times for substrate, syn diastereomer (both enantiomers) of product and anti diastereomer (both enantiomers) of product were 26.8 min., 20.4 min., and 22.2 min, respectively.

The separation of the two enantiomers of the syn and anti diastereomers was achieved by HPLC using dual columns connected in a series. The first column was a Pirkler column (DNBPG, dinitrophenylglycine) (250×4.6 mm, 5µ) and the second column was Chiralcel OB (250×4.6 mm, 5µ) (both columns purchased from J. T. Baker, Inc., Phillipsburg, N.Y.). The mobile phase consisted of 25:2.5:2.5:70 of isopropanol:n-butanol:methanol: hexane. The flow rate was 0.5 ml/min. and the detector wavelength was 230 nm. The retention times for the two enantiomers of syn were 20.1 min. and 23.3 min., respectively. The retention times for the two enantiomers of anti were 22 min. and 27.8 min., respectively.

The results obtained by using various microorganisms grown on Medium 1 and following the above procedure are shown in Table 1.

Batches were also further purified, subsequent to extraction, as exemplified by the following procedure:

The reduction product subsequent to extraction isolation (0.822 g) was dissolved in hot acetonitrile (16.5 ml) and the solution was filtered hot through a "D" sintered glass funnel. The filtrate was allowed to stand an room temperature (crystals formed quickly) for 45 minutes, and was then allowed to stand at 4° C. It was filtered and washed with cold acetonitrile. The crystals were air dried and weighed. $^1$H NMR in dimethylsulfoxide demonstrated that the crystals were essentially the syn material. (Crystal weight: 0.38 g; $[\alpha]^D 20$ (Cl, CHCl$_3$)=−21.7; $[\alpha]^D 20$ (Cl, CH$_3$OH)=−36.5).

The mother liquor residue (0.414 g) was dissolved in 7 ml of hot acetonitrile, filtered hot through a "D" sintered glass funnel and allowed to stand at room temperature for 2 hours. It was then placed in a cold room (4° C.) and left overnight. The crystals were then filtered and washed with cold acetonitrile (3×0.5 ml) and air dried giving 0.072 g as a second crop. $^1$H NMR was consistent with >98% syn.

Analysis indicated that the crystals obtained were approximately 100% optically pure Compound B.

TABLE 1

| Microorganism | Reaction Yield (syn compounds) (%)[1] | Optical Purity (Compound B) (%)[2] |
|---|---|---|
| Candida guilliermondii ATCC 20318 | 31 | 95 |
| Rhodococcus erythropolis ATCC 4277 | 39 | 96 |
| Saccharomyces cerevisiae ATCC 24702 | 35 | 94 |
| Hansenula polymorpha ATCC 26012 | 98 | 99.5 |
| Pseudomonas putida ATCC 11172 | 32 | 94 |
| Nocardia globerula ATCC 21505 | 36 | 92 |
| Mortierella ramanniana ATCC 38191 | 35 | 97 |
| Hansenula fabianii ATCC 58045 | 90 | 96 |

[1] Reaction yield calculated as:

$$\frac{[\text{combined amount of Compound B and Compound C}^{3/} \text{(syn enantiomer of Compound B)}]}{[\text{amount of starting material}]} \times 100$$

[2] Optical purity calculated as:

$$\frac{[\text{amount of Compound B}]}{[\text{combined amount of Compound B and Compound C}]} \times 100$$

[3] Compound C had the following structure:

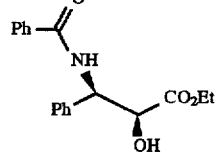

EXAMPLE 2

Use of Whole Cells: Variation in Reaction Time

The substrate for this process was Compound A. Of particular interest in this example was preparation of Compound B. Both Compounds A and B are described in Example 1.

Cells of Hansenula polymorpha ATCC 26012 were grown in 100 ml of Medium 1 combined in 500 ml flasks. Growth was carried out at 25° C. for 48 hours at 280 rpm. 100 ml of cultures were inoculated into 15 L of Medium 2 (see above for the composition thereof) combined in a fermentor. Growth in the fermentor was carried out at 25° C., 15 liters per minutes (LPM) aeration and 500 RPM agitation for 60 hours. Cells were harvested from the fermentor and used for the reduction ("biotransformation") of Compound A to Compound B.

Cells (200 grams) were suspended in 1 liter of 100 mM potassium phosphate buffer, pH 6.0 and homogenous cell suspensions were prepared. 2.5 grams of Compound A and 35 grams of glucose were added to the cell suspensions and the biotransformation of Compound A to Compound B was carried out at 22° C., 160 RPM for 24 hours. After 24 hours, an additional 35 grams of glucose were added and the biotransformation was continued for 72 hours at 22° C., 160 RPM. Samples were prepared and product yield and optical purity were determined as described in Example 1. The results obtained are summarized in Table 2 following.

TABLE 2

| Reaction Time (Hours) | Yield of syn compounds (%) | Optical Purity of Compound B (%) |
|---|---|---|
| 24 | 32 | — |
| 48 | 65 | — |
| 72 | 90 | 99.5 |

EXAMPLE 3

Use of Cell Extracts and Co-factor

The substrate for this process was Compound A as described above. Of particlar interest in this example was preparation of Compound B also described above.

Cells of *Hansenula polymorpha* ATCC 26012 were grown on Medium 1 and Medium 2 as described in Example 2.

Cells (150 grams) were suspended in 1.5 L of 0.2M potassium phosphate buffer, pH 6.0. The homogenized cell suspensions were disintegrated at 4° C. by a Microfluidizer at 13,000 psi pressure. The disintegrated cell suspension was centrifuged at 12,000 RPM for 30 minutes. The clear supernatant ("cell extract") was used for the biotransformation of Compound A to Compound B.

One liter of cell extract was supplemented with 2.5 grams of substrate (Compound A), formate dehydrogenase (500 units), 0.7 mM NAD$^+$ (nicotinamide adenine dinucleotide), and 25 grams of sodium formate. The reaction was carried out in a pH stat at pH 6.0, 150 RPM agitation, and 22° C. Periodically, samples were taken and analyzed for the reaction yield and optical purity of Compound B as described in Example 1. The results obtained are those shown in Table 3 following.

TABLE 3

| Reaction Time (Hours) | Compound B g/L | Yield (%) | Optical Purity (%) |
|---|---|---|---|
| 48 | 2.2 | 88 | >99% |

In the above procedure, the NADH cofactor used for the biotransformation of Compound A to Compound B was, concurrent with the biotransformation, formed and regenerated using formate dehydrogenase, NAD$^+$, and formate as shown below.

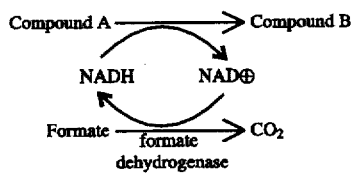

After complete conversion of Compound A to Compound B, the reaction mixture was adjusted to pH 7.0 and extracted three times with equal volumes of ethyl acetate. The organic phase was separated and washed twice with 0.7M sodium bicarbonate. The separated organic layer was dried over anhydrous sodium sulfate and ethyl acetate was removed under reduced pressure. The resulting oily residue was dried under vacuum at room temperature to recover a pale white solid in 85% yield (isolated) and 99% optical purity.

EXAMPLE 4

Use of Purified Oxido-Reductase

The substrate for this process (Compound A) was described in Example 1. Of particular interest in this example was the preparation of Compound B also described in Example 1.

Growth of *Hansenula polymorpha* ATCC 26012 was carried out on Medium 1 as described in Example 1. Cell extracts of *Hansenula polymorpha* ATCC 6012 were prepared as described in Example 3.

Cell extracts (700 ml) were loaded onto a DEAE-cellulose (DE-52) column and eluted with buffer containing sodium chloride in a linear gradient from 0 to 0.5M. Fractions containing oxido-reductase activity were pooled and concentrated by ammonium sulfate precipitation (70% saturation). Precipitated material was collected by centrifugation, dissolved in buffer, and loaded onto a Sephacryl S-200 column. Fractions containing reductase activity were pooled after chromatography and loaded onto a Mono-Q column. Proteins bound on the Mono-Q column were eluted with a buffer containing sodium chloride in a linear gradient from 0 to 0.5M. Fractions having oxido-reductase activity were pooled and analyzed by sodium dodecyl sulfate (SDS) gel electrophoresis. The purified enzyme was homogeneous. Overall, 250 fold purification was achieved.

The transformation of Compound A to Compound B was carried out by the purified enzyme (Mono-Q fraction). The reaction mixture in 20 ml of 0.1M potassium phosphate buffer (pH 6.0) contained 20 units of purified oxido-reductase enzyme, 200 mg of substrate (Compound A), 100 units of formate dehydrogenase, 1 gram of formate, and 50 mg of NAD$^+$. The reaction was carried out in a pH star at pH 6.0, 100 RPM agitation and 22° C. for 48 hours. Product (Compound B) and substrate (Compound A) concentrations were determined by the procedures described in Example 1. After 48 hours of reaction time, an 89% reaction yield and greater than 99% optical purity of Compound B was obtained.

EXAMPLE 5

Enzymatic Reduction

The substrate for this process (Compound A) is described in Example 1. Of particular interest in this example was the preparation of Compound B, also described in Example 1.

Commmercially available oxido-reductases (5–20 units) were suspended in 10 ml of 50 mM potassium phosphate buffer at pH 7.0. To the suspension NADH or NADPH (1.5 mg/ml) was added. The reaction was started by addition of 2 mg/ml of Compound A. The reaction was carried out at 25° C. at 150 RPM agitation for 48 hours. After 48 hours, samples were taken and analyzed for the reaction yield of Compound B as described in Example 1. The enzymes which produced Compound B and the reaction yields obtained are listed in the following Table 4.

TABLE 4

| Enzyme | Reaction Yield (syn compounds) |
|---|---|
| L-2-hydroxyisocaproate dehydrogenase | 20 |
| Lactic acid dehydrogenase | 10 |
| Yeast enzyme concentrate | 42 |
| β-hydroxybutyrate dehydrogenase | 5 |

EXAMPLE 6

The substrate (Compound A) and method of bioreduction employed for this example were the same as those of Example 1. The organisms used and the results obtained are listed in the following Table 5.

TABLE 5

| Organism | Syn %[1/] | Anti %[2/] |
|---|---|---|
| *Candida guilliermondii* ATCC 9058 | 18 | 82 |
| *Candida guilliermondi* ATCC 20318 | 30.8 | 69.2 |
| *Penicillium thomii* ATCC 14974 | 10 | 90 |
| *Rhodococcus rhodochorus* ATCC 19150 | 14.4 | 85.6 |
| *Rhodococcus rhodochorus* ATCC 14341 | 5.8 | 94.2 |
| *Mortierella alpina* ATCC 32221 | 11 | 89 |
| *Hansenula anomala* ATCC 8170 | 18.9 | 81.1 |
| *Cunninghamella echinulata* ATCC 26269 | 5.6 | 94 |
| *Pseudomonas putida* ATCC 11172 | 30.1 | 69.9 |
| *Nocardia salmonicolor* ATCC 19149 | 11 | 89 |
| *Geotrichum candidum* ATCC 34614 | 12.1 | 87.9 |
| *Norcardia globerula* ATCC 21505 | 35.5 | 64.5 |
| *Pichia pinus* ATCC 28780 | 31 | 72 |
| *Aspergillus versicolor* ATCC 26268 | 3.2 | 96 |
| *Mucor hiemalis* ATCC 8977B | 8 | 92 |

[1/]Syn % = $\frac{[\text{amount of Compound B and Compound C}]}{[\text{amount of starting material}]} \times 100$ that is, [% (B + C)]

[2/]Anti % = $\frac{[\text{amount of Compound D and Compound E (anti enantiomer of Compound D)}]}{[\text{amount of starting material}]} \times 100$ that is, [% (D + E)]

3/ Compound D had the structure:

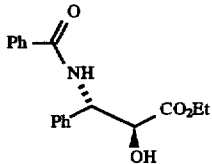

4/ Compound E had the structure:

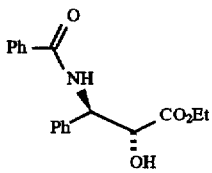

EXAMPLE 7

The substrate (Compound A) and method of enzymatic reduction employed for this example were those of Example 5. The commercially available enzymes used for this example, and the results obtained, are listed in the following Table 6.

TABLE 6

| Enzyme | Anti %[1/] |
|---|---|
| Glucose dehydrogenase | 88 |
| Alcohol dehydrogenase | 81 |
| Glycerol dehydrogenase | 72 |
| Formate dehydrogenase | 78 |
| β-hydroxybutyrate dehydrogenase | 90 |
| Pyruvate dehydrogenase | 92 |
| Hydroxy steroid dehydrogenase | 87 |

[1/]As defined above in Example 6.

What is claimed is:

1. A method for the enzymatic reduction of a compound of the formula I or a salt thereof:

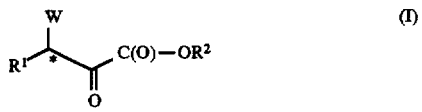

to form a compound of the formula II or a salt thereof:

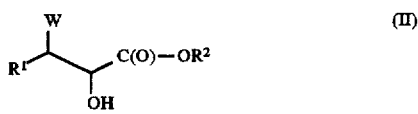

where

W is (a) —NHR$^3$; or (b) —N$_3$;

R$^1$ is aryl;

R$^2$ is (a) hydrogen; or (b) R$^4$, where R$^4$ is (i) alkyl; (ii) aryl; (iii) cycloalkyl; (iv) alkenyl; (v) alkynyl; or (vi) cycloalkenyl, wherein the ring portion of said cycloalkyl and cycloalkenyl groups consists of 1 to 3 rings and 3 to 7 carbons per ring; and R$^3$ is (a) —C(O)—OR$^4$, where R$^4$ is alkyl; or (b) —C(O)—R$^4$, where R$^4$ is aryl;

where, with respect to the chiral center marked with an asterisk, said compound of the formula I or salt thereof is employed as a starting material as a single isomer or as a mixture of both R and S isomers, comprising the step of contacting said compound of the formula I or salt thereof with an enzyme or microorganism which catalyzes said reduction, and effecting said reduction, thereby obtaining said compound of the formula II or salt thereof, (1) wherein said enzyme or microorganism is a microorgsnism selected from the genera consisting of Candida, Rhodococcus, Saccharomyces, Hansenula, Pseudomonas, Nocardia, Mortierella, Penicillium, Cunninghamella, Geotrichum, Pichia, Aspergillus, and Mucor, or is an enzyme obtained therefrom, or (2) wherein said enzyme is selected from the group consisting of L-2-hydroxy isocaproate dehydrogenase, lactic acid dehydrogenase, β-hydroxyhutyrate dehydrogenase, glucose dehydrogenase, alcohol dehydrogenase, glycerol dehydrogenase, formate dehydrogenase, pyruvate dehydrogenase and hydroxy steroid dehydrogenase.

2. The method of claim 1, wherein said compound of the formula I or salt thereof is reduced to preferentially form the following compounds IIa and/or IIb or salts thereof:

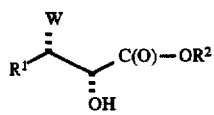
(IIa)

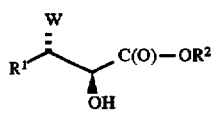
(IIb)

3. The method of claim 2, comprising the step of contacting said compound of the formula I or salt thereof with said enzyme or microorganism which catalyzes stereoselective reduction thereof to form a compound of the formula IIa or salt thereof, and effecting said stereoselective reduction.

4. The method of claim 2, comprising the step of contacting said compound of the formula I or salt thereof with said enzyme or microorganism which catalyzes stereoselective reduction thereof to form a compound of the formula IIb or salt thereof, and effecting said stereoselective reduction.

5. The method of claim 1, wherein W is —$NHR^3$.

6. The method of claim 5, wherein W is arylcarbonylamino.

7. The method of claim 6, wherein W is benzoylamino.

8. The method of claim 7, wherein $R^1$ is phenyl and $R^2$ is alkyl.

9. The method of claim 5, wherein W is alkyloxycarbonylamino.

10. The method of claim 9, wherein W is t-butyloxycarbonylamino.

11. The method of claim 10, wherein $R^1$ is phenyl and $R^2$ is alkyl.

12. The method of claim 1, wherein, with respect to the chiral center marked with an asterisk, both the R and S isomers of the compound of formula I are employed as the starting material in said method.

13. The method of claim 12, wherein a racemate of R and S enantiomers is employed as said starting material.

14. The method of claim 1, wherein, with respect to the chiral center marked with an asterisk, a single R or S stereoisomer, but not both, of the compound of the formula I is employed as the starting material in said method.

15. The method of claim 1, wherein said enzyme or microorganism is a microorganism selected from the group consisting of Nocardia globerula, Penicillium thomii, Rhodococcus rhodochrous, Mortierella alpina, Hansenula anomala, Cunninghamella echinulata, Nocardia salmonicolor, Geotrichum candidum, Pichia pinus, Aspergillus versicolor, Mucor hiemalis, Candida guilliermondii, Rhodococcus erythropolis, Saccharomyces cerevisiae, Pseudomonas putida and Mortierella ramanniana, or is an enzyme obtained therefrom.

16. The method of claim 15, wherein said enzyme or microorganism is a microorganism selected from the group consisting of Nocardia globerula ATCC 21505, Candida guilliermondii ATCC 20318 and ATCC 9058, Rhodococcus erythropolis ATCC 4277, Saccharomyces cerevisiae ATCC 24702, Pseudomonas putida ATCC 11172, Mortierella ramanniana ATCC 38191, Penicillium thomii ATCC 14974, Rhodococcus rhodochrous ATCC 19150 and ATCC 14341, Mortierella alpina ATCC 32221, Hansenula anomala ATCC 8170, Cunninghamella echinulata ATCC 26269, Nocardia salmonicolor ATCC 19149, Geotrichum candidum ATCC 34614, Pichia pinus ATCC 28780, Aspergillus versicolor ATCC 26268, and Mucor hiemalis ATCC 8977B, or is an enzyme obtained therefrom.

17. The method of claim 1, wherein said enzyme or microorganism is a microorganism of the species Hansenula polymorpha or Hansenula fabianii, or is an enzyme obtained therefrom.

18. The method of claim 17, wherein the microorganism Hansenula polymorpha ATCC 26012, or an enzyme obtained therefrom, or the microorganism Hansenula fabianii ATCC 58045, or an enzyme obtained therefrom, is used.

19. The method of claim 1, wherein said enzyme (2) is L-2-hydroxy isocaproate dehydrogenase, lactic acid dehydrogenase, β-hydroxybutyrate dehydrogenase, glucose dehydrogenase, alcohol dehydrogenase, glycerol dehydrogenase, formate dehydrogensse, pyruvate dehydrogenase or hydroxy steroid dehydrogenase.

20. The method of claim 1 further comprising, subsequent to said reduction, a separation step wherein said compound of the formula II is separated from other components of the reaction medium.

21. The method of claim 20, wherein said separation step is an extraction, distillation, crystallization, or column chromatography step.

22. The method of claim 21, wherein said separation step is an extraction step.

23. The method of claim 21, wherein said separation step is a crystallization step.

24. The method of claim 21, wherein said separation step is a column chromatography step.

25. The method of claim 1, wherein said compound of the formula I is racemic 2-keto-3-(N-benzoylamino)-3-phenylpropionic acid ethyl ester, and said compound of the formula II is (2R,3S)-(−)-N-benzoyl-3-phenyl-isoserine ethyl ester.

* * * * *